United States Patent [19]

Miya, deceased et al.

[11] 4,278,567

[45] Jul. 14, 1981

[54] PROCESS FOR PREPARATION OF COPPER-IRON-ALUMINUM HYDROGENATION CATALYST

[75] Inventors: Bunji Miya, deceased, late of Wakayama, Japan, by Kazu Miya, heir; by Fumiaki Miya, heir, Tokyo, Japan; by Yukiko Nawashiro, heir, Ishikawa, Japan

[73] Assignee: Kao Soap Co., Ltd., Tokyo, Japan

[21] Appl. No.: 128,985

[22] Filed: Mar. 10, 1980

[30] Foreign Application Priority Data

Mar. 30, 1979 [JP] Japan .................................. 54-377741

[51] Int. Cl.³ .................... B01J 21/04; B01J 23/72; B01J 23/74
[52] U.S. Cl. .................................. 252/466 J; 568/885
[58] Field of Search ...................... 252/466 J; 568/885

[56] References Cited

U.S. PATENT DOCUMENTS 4,144,198   3/1979   Miya et al. .................... 252/466 J

*Primary Examiner*—W. J. Shine
*Attorney, Agent, or Firm*—Blanchard, Flynn, Thiel, Boutell & Tanis

[57] ABSTRACT

A process for the preparation of copper-iron-aluminum hydrogenation catalysts comprises the step of: dissolving a cupric salt, a ferrous salt and an aluminum salt in water dissolving urea in the resulting aqueous solution in such an amount that the mole number of urea is at least 0.7 time as large as the sum of equivalents of the metal ions, heating the mixed aqueous solution, further continuing the heating until a pH of the liquid is 4.6 to 7.5, adding an alkali to the reaction liquid to elevate a pH to 9.5 to 11.5, further conducting the reaction and then separating, water-washing, drying and calcining the formed precipitate.

5 Claims, No Drawings

PROCESS FOR PREPARATION OF COPPER-IRON-ALUMINUM HYDROGENATION CATALYST

BACKGROUND OF THE INVENTION

1. Field of the Invention

The present invention relates to a process for the preparation of copper-iron-aluminum hydrogenation catalysts.

2. Description of Prior Arts

Linear higher alcohols are prepared by reducing methyl esters of fatty acids with high pressure hydrogen at a high temperature. A copper-chromium oxide catalyst is used for this reaction, and this catalyst is ordinarily called "copper chromite catalyst." Few developments have been made to the process for the preparation of this catalyst disclosed in Industrial and Engineering Chemistry, 26, page 878 (1936). This process comprises adding ammonia to a dichromate dissolved in water, adding a cupric salt to the mixture, recovering the formed precipitate by filtration and water-washing, drying and calcining the recovered precipitate. In this process, the reaction among the reactants is insufficient, and this process has a fatal defect that copper ions and large quantities of hexavalent chromium ions are discharged at the filtering and water-washing steps. In order to prevent environmental pollution, these heavy metals are trapped according to appropriate methods, but no decisive method for disposal of the formed heavy metal-containing sludges has been established.

As means for solving this problem, we previously proposed a process for preparing copper-iron-aluminum catalysts, which comprises dissolving a cupric salt, a ferrous salt and an aluminum salt in water, adding an alkali to the solution at a temperature higher than 60° C. to form a precipitate, and separating, water-washing, drying, calcining and pulverizing the precipitate (see Japanese Patent Application Laid-Open Specification No. 92395/78). We also proposed a process for preparing copper-iron-aluminum catalysts, which comprises dropping simultaneously a mixed aqueous solution of a cupric salt, a ferrous salt and an aluminum salt and an alkali aqueous solution to a reaction vessel, agitating the mixture at a temperature higher than 50° C. for 10 minutes to 10 hours after completion of the dropping, and separating, water-washing, drying and calcining the formed precipitate (see Japanese Patent Application No. 80663/78). The copper-iron-aluminum catalysts prepared according to the processes disclosed in the specifications of these patent applications are comparable or superior to the conventional copper chromite catalyst with respect to the activity, selectivity, durability and other properties. However, it has been found that the catalysts prepared according to the processes disclosed in these patent specifications have a defect that since the filtering speeds of these catalysts are very low when they are separated from the reaction products by filtration after the hydrogenation, a large filtering apparatus should be used for separation of the catalysts from the reaction products.

SUMMARY OF THE INVENTION

The present invention is to provide a process for preparing copper-iron-aluminum hydrogenation catalysts in which the defect of the copper chromite catalyst is eliminated and simultaneously, the above-mentioned problem of the low filtering speed is solved. More specifically, in accordance with the present invention, there is provided a process for the preparation of copper-iron-aluminum catalysts, which comprises heating a mixed aqueous solution of a cupric salt, a ferrous salt, an aluminum salt and urea to precipitate copper, iron and aluminum from the above 3 metal salts by ammonium formed from urea by heating, adding dropwise an aqueous solution of an alkali metal hydroxide to the reaction liquid to elevate the pH of the reaction liquid, then conducting the reaction for a predetermined time, recovering the precipitate by filtration, water-washing and drying the recovered precipitate, and calcining the dried precipitate.

The process for preparing catalysts according to the present invention will now be described in detail.

Various cupric salts may be used in the present invention. For example, cupric sulfate, cupric chloride and cupric nitrate can be used. From the viewpoint of the price, cupric sulfate is most preferred. Ferrous sulfate, ferrous chloride, ferrous nitrate and the like may be used as the ferrous salt, and for the same reason as described above, ferrous sulfate is most preferred. The ferrous salt that is used in the present invention should not contain a ferric salt. If a ferric salt is included, the above-mentioned filtering property is drastically degraded. Accordingly, when an industrial ferrous salt containing a small amount of a ferric salt is used, it is necessary to reduce this salt in advance according to an appropriate method. As the aluminum salt, there may be used aluminum sulfate, aluminum chloride, aluminum nitrate and various alums. Among them, aluminum sulfate is most preferred. In the process of the present invention, industrial refined urea having a purity as high as possible should be used as urea for formation of precipitates.

In the mixed aqueous solution of the copper, iron and aluminum salts, the atomic ratios of iron and aluminum to copper are 0.4–2.5 and 0.1–3.0 respectively, and preferably 0.4–2.5 and 0.1–2.0, respectively. If the atomic ratios are outside these ranges, the activity of the resulting catalyst is low and occurrence of side reactions becomes conspicuous at the hydrogenation reaction. Urea is used in such an amount that the mole number of urea is at least 0.7, preferably 1.0, time the sum of equivalents of the metal ions. The upper limit of the amount of urea is not particularly set, but if urea is used in too much an amount, the process becomes disadvantageous from the economical viewpoint. It is preferred that urea be used in such an amount that the mole number of urea is 1.2 to 3 times, especially 1.8 to 3 times, as large as the sum of equivalents of the metal ions.

The concentration of the aqueous solution formed by dissolving the foregoing 4 starting materials in water has serious influences on the properties of the resulting catalyst. Ordinarily, the lower is the concentration, the better are the properties of the resulting catalyst. However, from the industrial and economical viewpoints, optimum concentrations should naturally be determined. Referring to the copper salt concentration, an optimum concentration is obtained when 0.07 to 0.8 mole, especially 0.25 to 0.4 mole, of the copper salt is dissolved in 900 ml of water.

When the mixed aqueous solution of the copper, iron and aluminum salts and urea is heated, urea is gradually decomposed to form ammonia and carbon dioxide. Carbon dioxide escapes from the reaction system, but ammonia immediately reacts with the metal salts to form three metal hydroxides and ammonium sulfate. The metal hydroxides further undergo complicated changes, which have not been clarified. When a small amount of air is blown during this reaction, a black homogeneous precipitate is obtained. However, if air is not blown, a minute amount of a brown precipitate is sometimes formed as the by-product in addition to the black precipitate. This brown precipitate, however, has no substantial influence on the catalytic activity of the resulting catalyst.

The precipitate-forming speed is greatly changed depending on the temperature. If the temperature is elevated by 5° C., the speed is substantially doubled. A temperature lower than 90° C. is not preferred from the practical viewpoint and the catalytic activity of the catalyst prepared at such low temperature is not good. Accordingly, it is preferred that the reaction temperature be higher than 90° C. The upper limit of the reaction is not critical, but if the reaction is carried out under atmospheric pressure, it is preferred that the reaction temperature be up to about 103° C. And the reaction may be carried out at further elevated temperatures under a pressure in order to obtain a shorter reaction time.

When urea is decomposed and the pH is about 3.7 (as determined at room temperature; all the pH values given hereinafter are those as determined at room temperature), a white precipitate is formed. At a pH of about 4.6, this precipitate is abruptly blackened through a yellowish green color and a brown color. The reaction is further conducted until the pH is 4.6 to 7.5, preferably 5 to 7.5, more preferably 6 to 6.5. When urea is used in an amount 2 times the stoichiometric amount and the reaction temperature is controlled to 100° C., 4 to 5 hours are required for elevating the pH to 6.5.

When the pH value of the reaction liquid arrives at a predetermined level, an aqueous solution of an alkaline agent is dropped to the reaction liquid while maintaining the temperature above 60° C. As an alkaline agent, alkali-metal hydroxide is preferred and sodium hydroxide is most preferred as the alkali metal hydroxide from the viewpoint of the price. The concentration of the alkali metal hydroxide is adjusted to an appropriate level, for example, 30%. The dropping addition is conducted while the reaction liquid is being sufficiently agitated, and is completed within about 30 minutes. At the point of termination of the dropwise addition, the pH value of the reaction liquid should be 9.5 to 11.5, preferably 10 to 10.5. Ammonia gas is produced simultaneously with the dropwise addition of the alkali metal hydroxide. This ammonia gas should be discharged from the reaction system together with water vapor. If ammonia gas is thus removed, an ammonia-copper complex salt formed in the reaction liquid is gradually decomposed. This complex salt is decomposed substantially completely within 30 minutes to 1 hour from the point of termination of the dropwise addition of the alkali metal hydroxide, and the filtrate of the reaction liquid becomes colorless. If the decomposition is not completed, the filtrate has a bluish color. The reaction time after the point of termination of the dropwise addition of the alkali metal hydroxide is 30 minutes to 5 hours, preferably about 2 hours.

After completion of the above reaction, the precipitate is separated from the mother liquor. Any of customary methods may optionally be adopted for this separation, and separation can be accomplished very easily by application of a customary filtering method. It is ordinarily difficult to separate a hydroxide precipitated from a metal salt by an alkali according to a customary filtering method. However, a precipitate gradually formed by ammonia produced by decomposition of urea can easily be filtered. The precipitate recovered by filtration is water-washed several times to remove sodium sulfate formed as a by-product. This water washing can be accomplished very easily, and the water content in the cake left after water washing is lower than 35%. Sodium sulfate is appropriately removed by crystallization from the mother liquor left after separation of the precipitate, and the residual liquid can be used as water for the next reaction, whereby urea used in an excessive amount can be effectively utilized.

The water-washed precipitate is dried according to a customary method and is then calcined. The calcination is carried out at a temperature of 550° to 800° C., preferably 600° to 750° C., especially preferably about 650° C. The calcination time is not particularly critical, but from the economical viewpoint, it is preferred that the calcination time be shorter than 10 hours. The calcination product can be used directly as a catalyst without pulverization.

The catalyst prepared according to the above-mentioned process of the present invention is comparable or superior to the copper chromite catalyst with respect to the activity, selectivity, durability and filtering property, and is very suitable for industrial application.

The present invention will now be described with reference to the following Examples.

EXAMPLE 1

In 900 ml of water were dissolved 62.42 g of $CuSO_4.5H_2O$, 97.28 g of $FeSO_4.7H_2O$, 91.63 g of $Al_2(SO_4)_3.18H_2O$ and 121.62 g of urea. The Cu/Fe/Al atomic ratio was 1/1.4/1.1, and the amount of urea was 2 times the stoichiometric amount. The solution was charged in a reaction vessel equipped with a reflux cooler and air was circulated through the reaction vessel at a rate of 30 l per hour. The temperature of the solution was elevated to 100° C. to initiate the reaction. With decomposition of urea, the pH value was gradually elevated, and the liquid which was initially bluish green and transparent was converted to a liquid containing a yellowish green precipitate for about 30 minutes from the point of initiation of the reaction. When 1 hour and 20 minutes had passed from the start of the reaction, this precipitate was abruptly blackened. At this point, the pH value was 4.6. The pH value was once reduced to 4.3 and was then elevated again. When the reaction was conducted for 4 hours and 50 minutes, the pH was 6.5. The reflux cooler was separated from the reaction vessel, and 270 g of a 30% aqueous solution of NaOH was added dropwise to the reaction liquid over a period of 30 minutes. The pH of the reaction liquid was elevated to 10.5. Simultaneously with the dropwise addition, ammonia gas was produced, and this ammonia gas was removed from the reaction vessel together with water vapor. After completion of the dropwise addition of NaOH, the reaction was further conducted at 100° C. for 2 hours while maintaining the pH at 10.5 by adding a small amount of NaOH continuously. The total amount of distilled ammonia and water was about 700 g. Water was successively supplied to the reaction vessel to compensate 700 g of distilled ammonia and water. After completion of the reaction, the reaction liquid was filtered under suction. Filtration could be accomplished very easily. The filtrate was colorless. The precipitate was washed with 660 ml of water 5 times and was then dried according to customary procedures. The drying treatment was completed within a very short time very easily. The dried precipitate was directly heated at 650° C. for 1 hour in air without preliminary pulverization to obtain an intended catalyst.

To 200 g of a methyl ester of coconut fatty acid was added 6 g of the so obtained catalyst, and hydrogenation was carried out at a temperature of 275° C. under a hydrogen pressure of 150 kg/cm$^2$ in an autoclave having a capacity of 500 ml. In order to remove methanol formed by the reaction, the gas in the autoclave was discharged at intervals of 30 minutes and fresh hydrogen was supplied. When 30 minutes, 90 minutes, 150 minutes, 180 minutes and 210 minutes had passed from the point of initiation of the reaction, small amounts of samples were collected, and after washing, the saponification values were determined and the amounts of by-products (hydrocarbons, ethers and secondary alcohols) were measured by gas chromatography. From the saponification values $S_1$ and $S_2$ of the samples collected at the points of 30 minutes and 90 minutes, the first-order reaction rate constant K (1/hr) was calculated according to the formula of $K = \ln[(S_1-8)/(S_2-8)]$. In this formula, the numerical value of 8 is an equilibrium saponification value obtained at 275° C. and 150 Kg/cm$^2$. From the amounts of by-products formed after the point of 120 minutes, the zero-order reaction rate constant K(%/hr) was determined. It was found that K was 3.21 and B was 1.04. When the same experiment was carried out by using a copper chromite catalyst having a highest quality available, it was found that K was 3.14 and B was 1.44. The ratio B/K (=R) is a relative value indicating the speed of formation of by-products when the reaction speed is made equal by adjusting the amount of the catalyst. It was found that R was 0.324 in the case of the catalyst of this Example and R was 0.459 in case of the copper chromite catalyst. Thus, it was confirmed that the catalyst of this Example was excellent in the selectivity.

The liquid left after hydrogenation of the ester was diluted with dodecyl alcohol so that the catalyst concentration was 1%, and the filtration speed constant F (m$^2$/hr) under certain conditions (filtration pressure of 3 Kg/cm$^2$ and temperature of 50° C. ) was determined. It was found that in case of the catalyst of this Example, F was 1.90 and in case of the copper chromite catalyst, F was 1.32. Thus, it was confirmed that the catalyst of this Example was excellent in the filtering property.

EXAMPLE 2

A catalyst was prepared in the same manner as described in Example 1 except that 68.10 g of CuSO$_4$.5H$_2$O, 90.96 g of FeSO$_4$.7H$_2$O, 118.14 g of Al$_2$(SO$_4$)$_3$.18H$_2$O and 135.81 g of urea were dissolved in 900 ml of water. The atomic ratio of Cu/Fe Al was 1/1.2/1.3. The value K determined in the same manner as in Example 1 was 2.91 and the value R was 0.362.

To 150 g of a methyl ester of coconut oil fatty acid was added 7.5 g of the so obtained catalyst, and the reaction was carried out at a temperature of 275° C. under a hydrogen pressure of 250 Kg/cm$^2$ for 2.5 hours. The catalyst was separated and recovered from the reaction mixture by centrifugal separation and was used again for the same reaction. After the reaction was thus repeated 7 times, the value K was slightly reduced and was 2.75. Thus, the activity was slightly reduced, but the value R was 2.66 and was improved over the value R obtained at the first reaction. Thus, it was found that the catalyst had a good durability. The same experiment was conducted by using a copper chromite catalyst. It was found that at the first reaction, K was 3.14 and R was 0.459, and that after the reaction was repeated 7 times, K was 2.97 and R was 0.287.

EXAMPLE 3

In 450 ml of water were 97.28 g of FeSo$_4$.7H$_2$O of the industrial grade and 2 g of hydrazine sulfate, and the solution was heated at 95° to 100 ° C. for 30 minutes under a nitrogen gas current to reduce Fe(III) contained in the ferrous sulfate to Fe(II). By using the so treated ferrous sulfate and chemicals of the industrial grades as other starting materials, a catalyst was prepared in the same manner as described in Example 1. It was found that K was 3.00, R was 0.427 and F was 3.61. When the hydrazine treatment was not conducted, F was 0.046 and separation of the catalyst by filtration was very difficult.

EXAMPLES 4 THROUGH 7

Catalysts were prepared in the same manner as described in Example 1 except that the Cu/Fe/Al atomic ratio was changed as indicated in Table 1. Obtained results are shown in Table 1.

TABLE 1

|  | Example 4 | Example 5 | Example 6 | Example 7 |
|---|---|---|---|---|
| CuSO$_4$ . 5H$_2$O, g | 68.10 | 62.42 | 57.62 | 53.51 |
| FeSO$_4$ . 7H$_2$O, g | 90.96 | 97.28 | 102.62 | 107.21 |
| Al$_2$(SO$_4$)$_3$ . 18H$_2$O, g | 81.79 | 124.96 | 99.96 | 64.26 |
| Urea, g | 116.38 | 139.80 | 126.11 | 106.65 |
| Cu/Fe/Al Atomic Ratio | 1/1.2/0.9 | 1/1.4/1.5 | 1/1.6/1.3 | 1/1.8/0.9 |
| K | 2.78 | 2.73 | 3.31 | 2.54 |
| R | 0.361 | 0.373 | 0.400 | 0.408 |

What is claim is:

1. A process for the preparation of a copper-iron-aluminum hydrogenation catalyst, which comprises the steps of: dissolving a cupric salt, a ferrous salt and an aluminum salt in water so that the Cu/Fe/Al atomic ratio is 1/(0.4–2.5)/(0.1–3.0), dissolving urea in the resulting aqueous solution in such an amount that the mole number of urea is at least 0.7 time as large as the sum of the equivalents of the metal ions of said salts, heating said aqueous solution until the pH of the liquid is 4.6 to 7.5, adding an alkali to the reaction liquid to elevate the pH to 9.5 to 11.5, further conducting the reaction and then separating, water-washing, drying and calcining the formed precipitate.

2. A process as claimed in claim 1, in which said alkali is an alkali metal hydroxide.

3. A process for the preparation of a copper-iron-aluminum hydrogenation catalyst, which comprises the steps of: dissolving a cupric salt, a ferrous salt and an aluminum salt in water so that the Cu/Fe/Al atomic ratio is 1/(0.4–2.5)/(0.1–3.0), dissolving urea in the resulting aqueous solution in such an amount that the mole number of urea is at least 0.7 time as large as the sum of the equivalents of the metal ions of said salts, heating said aqueous solution at a temperature higher than 90° C. to precipitate copper, iron and aluminum, further continuing the heating until the pH of the liquid is 4.6 to 7.5, adding an alkali metal hydroxide to the reaction liquid to elevate the pH to 9.5 to 11.5, further conducting the reaction at a temperature higher than 60° C. for 30 minutes to 5 hours, separating, water-washing and drying the formed precipitate and calcining the dried precipitate at a temperature of from 550° C. to 800° C.

4. A process for the preparation of a copper-iron-aluminum hydrogenation catalyst, which comprises the steps of: dissolving a cupric salt, a ferrous salt and an aluminum salt in water so that the Cu/Fe/Al atomic ratio is 1/(0.4–2.5)/(0.1–2.0), dissolving urea in the resulting aqueous solution in such an amount that the mole number of urea is at least 1.0 time as large as the sum of the equivalents of the metal ions of said salts, heating said aqueous solution at a temperature higher than 90° C. to precipitate copper, iron and aluminum, further continuing the heating until the pH of the liquid is 5 to 7.5, adding an alkali metal hydroxide to the reaction liquid to elevate the pH to 9.5 to 11.5, further conducting the reaction at a temperature higher than 60° C. for 30 minutes to 5 hours, separating, water-washing and drying the formed precipitate and calcining the dried precipitate at a temperature of from 550° C. to 800° C.

5. A process as claimed in claim 1, claim 3 or claim 4 wherein the cupric salt is cupric sulfate, the ferrous salt is ferrous sulfate and the aluminum salt is aluminum sulfate.

* * * * *

UNITED STATES PATENT AND TRADEMARK OFFICE
CERTIFICATE OF CORRECTION

PATENT NO. : 4 278 567
DATED : July 14, 1981
INVENTOR(S) : Bunji Miya, deceased, et al It is certified that error appears in the above—identified patent and that said Letters Patent is hereby corrected as shown below:

Under "Foreign Application Priority Data" change "54-377741" to ---54-37774---.

Signed and Sealed this

Seventeenth Day of November 1981

[SEAL]

Attest:

Attesting Officer

GERALD J. MOSSINGHOFF

Commissioner of Patents and Trademarks